US010517766B2

(12) United States Patent
Robinson et al.

(10) Patent No.: US 10,517,766 B2
(45) Date of Patent: Dec. 31, 2019

(54) FOAM DRESSING WITH INTEGRAL POROUS FILM

(71) Applicant: KCI Licensing, Inc., San Antonio, TX (US)

(72) Inventors: Timothy Mark Robinson, Shillingstone (GB); Paul S. Slack, San Jose, CA (US); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 552 days.

(21) Appl. No.: 15/043,974

(22) Filed: Feb. 15, 2016

(65) Prior Publication Data

US 2016/0158068 A1 Jun. 9, 2016

Related U.S. Application Data

(60) Continuation of application No. 14/015,385, filed on Nov. 13, 2013, now Pat. No. 9,289,328, which is a division of application No. 13/316,997, filed on Dec. 12, 2011, now Pat. No. 8,613,733.

(60) Provisional application No. 61/423,405, filed on Dec. 15, 2010.

(51) Int. Cl.
*A61F 13/00* (2006.01)
*A61F 13/02* (2006.01)

(52) U.S. Cl.
CPC .. *A61F 13/00068* (2013.01); *A61F 13/00987* (2013.01); *A61F 13/00995* (2013.01); *A61F 13/02* (2013.01); *A61F 2013/0017* (2013.01); *A61F 2013/0054* (2013.01); *A61F 2013/00174* (2013.01); *A61F 2013/00536* (2013.01); *A61F 2013/00587* (2013.01)

(58) Field of Classification Search
CPC ..................... A61F 13/00987; A61F 13/00995
See application file for complete search history.

(56) References Cited

U.S. PATENT DOCUMENTS

| 1,355,846 A | 10/1920 | Rannells |
| 2,547,758 A | 4/1951 | Kelling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |

(Continued)

FOREIGN PATENT DOCUMENTS

| AU | 550575 B2 | 3/1986 |
| AU | 745271 B2 | 3/2002 |

(Continued)

OTHER PUBLICATIONS

Canadian Examiner's Report for corresponding Application No. 2819882, dated Apr. 20, 2018.

(Continued)

*Primary Examiner* — Adam Marcetich
*Assistant Examiner* — Jessica R Arble

(57) ABSTRACT

Wound dressings and wound inserts including a porous film layer and at least a channel, forming wound inserts including a porous film layer and at least a channel, and wound-treatment wound inserts.

14 Claims, 4 Drawing Sheets

(56) References Cited

U.S. PATENT DOCUMENTS

| | | |
|---|---|---|
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A * | 5/1983 | Svedman .......... A61F 13/00068 604/114 |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,466,231 A * | 11/1995 | Cercone .................. A61F 13/36 602/41 |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,626,814 A | 5/1997 | Vicino |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0243043 A1 | 12/2004 | McCarthy et al. |
| 2007/0185426 A1 | 8/2007 | Ambrosio et al. |
| 2009/0018479 A1 | 1/2009 | McCarthy et al. |
| 2009/0264549 A1 * | 10/2009 | Brown .................. A47L 13/16 521/172 |
| 2009/0287129 A1 * | 11/2009 | Boehringer ....... A61F 13/00021 602/43 |
| 2009/0293887 A1 * | 12/2009 | Wilkes .................. A61L 15/60 128/888 |
| 2014/0163491 A1 | 6/2014 | Schuessler et al. |
| 2015/0080788 A1 | 3/2015 | Blott et al. |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 1574066 A * | 9/1980 | ............. A61B 5/201 |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 93/009727 A1 | 5/1993 | |
| WO | 94/020041 A1 | 9/1994 | |
| WO | WO 9420152 A1 * | 9/1994 | .......... A61M 1/0084 |

(56) References Cited

FOREIGN PATENT DOCUMENTS

| WO | 96/05873 A1 | 2/1996 |
| WO | 97/18007 A1 | 5/1997 |
| WO | 0061206 A1 | 10/2000 |
| WO | 2009158124 A1 | 12/2009 |
| WO | 2009158128 A2 | 12/2009 |
| WO | 2010033613 A1 | 3/2010 |
| WO | 2011090991 A2 | 7/2011 |

OTHER PUBLICATIONS

Japanese Notice of Rejection for Corresponding Application No. 2017066931, dated Apr. 17, 2018.

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., MD., et al; "Effective Management of incisional and cutaneous fistulae with closed suction wound drainage"; Contemporary Surgery, vol. 34, Jun. 1989, pp. 59-63.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A.C.® Therapy Clinical Guidelines: A Reference Source for Clinicians; Jul. 2007.

* cited by examiner

FOAM DRESSING WITH INTEGRAL POROUS FILM

CROSS-REFERENCE TO RELATED APPLICATION

This application is a continuation of U.S. patent application Ser. No. 14/015,385, filed Nov. 13, 2013, which is a divisional of U.S. patent application Ser. No. 13/316,997, filed Dec. 12, 2011, which claims priority to U.S. Provisional Patent Application No. 61/423,405, filed Dec. 15, 2010. Each of the above-referenced applications are incorporated herein by reference for all purposes.

BACKGROUND

1. Field of the Invention

The present invention relates generally to healing of wounds and wound-treatment therapies. More particularly, but not by way of limitation, the present invention relates to fluid-instillation and negative-pressure wound therapies.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape). Instillation fluids (e.g., irrigation fluids and/or medicaments) may be used in conjunction with negative pressure wound therapy to promote healing and/or improve efficacy. One example of a system for delivering active solutions to a wound is disclosed in U.S. Pat. No. 6,398,767.

In certain applications, providing negative pressure to the wound site is clinically advantageous, but formation of granulation tissue is undesirable. For example, providing negative pressure to orthopedic cavity wounds containing hardware such as plates, rods, or pins may help these wounds heal faster. However, the formation of granulation tissue around this hardware can be harmful.

SUMMARY

Wound inserts, and methods for making and using them, are presented.

Some embodiments of a method of manufacturing a wound insert comprise obtaining a member comprising open-celled reticulated foam, the member further comprising a first surface, a second surface, and an uncompressed thickness; obtaining a platen press comprising a first platen and a second platen; heating the first platen to a first temperature; placing the member in the platen press such that the first surface faces the first platen and the second surface faces the second platen; and compressing the member to a compressed thickness for a compression time.

Additionally, some embodiments may further comprise the step of forming a porous film layer on the first surface of the member. Other embodiments may further comprise the step of forming a porous film layer on the second surface of the member. Still other embodiments may further comprise removing a portion of the porous film layer from the first surface. The removing step may comprise laser cutting, laser etching, die cutting, or water cutting. Still other embodiments may further comprise forming channels in the porous film layer.

In certain embodiments, the compressed thickness is less than about one-tenth, one-ninth, one-eighth, one-seventh, one-sixth, or one-fifth the uncompressed thickness. In some embodiments, the uncompressed thickness is about 0.5 inch and the compressed thickness is about 0.05 inch. In some embodiments, the first platen, the second platen, or both may be heated to a temperature between about 160° C. and about 180° C.; in specific embodiments, the platen may be heated to a temperature of about 175° C. The compression time may between about 15 minutes and about 30 minutes.

In some embodiments, the member may comprise polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member may comprise a bioabsorbable polymer, examples of which include polylactic acid, polylactide (PLA), polyglycolic acid, polyglycolide (PGA), and polycaprolactone (PCL).

Other embodiments of a method of manufacturing a wound insert comprise the steps of: obtaining an open-celled reticulated foam member having a first surface, a second surface, and a thickness between the first and second surfaces; felting the first surface of the member to form a felted layer; and forming at least one channel in the felted layer.

In certain embodiments, the at least one channel may be in fluid communication with the second layer through the thickness. The felting step may further comprise applying heat and pressure to the member. In some embodiments, forming may comprise laser cutting, water cutting, or die cutting.

The member may comprise polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member may comprise a bioabsorbable polymer, examples of which include polylactic acid, polylactide (PLA), polyglycolic acid, polyglycolide (PGA), and polycaprolactone (PCL).

Certain embodiments are directed to a wound insert. Some embodiments comprise open-celled reticulated foam comprising a first surface, a second surface and a thickness between the first and second surfaces, wherein the first surface of the open-celled reticulated foam comprises a porous film layer and at least one channel.

Embodiments of a wound insert may comprise polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member may comprise a bioabsorbable polymer, examples of which include polylactic acid, polylactide (PLA), polyglycolic acid, polyglycolide (PGA), and polycaprolactone (PCL).

Other embodiments of a wound insert may comprise an open-celled reticulated foam member comprising a porous film layer, the porous film layer comprising a film thickness; and at least a channel in the porous film layer, wherein the at least one channel comprises a channel depth, the channel depth being equal to or greater than the film thickness; where the wound insert is configured to be disposed between a wound of a patient and a drape coupled to the skin adjacent to the wound.

Specific embodiments may further comprise at least a sealed edge joining first and second surfaces. In various embodiments, the open-celled reticulated foam member may comprise polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member may comprise a bioabsorbable polymer, examples of which include polylactic acid, polylactide (PLA), polyglycolic acid, polyglycolide (PGA), and polycaprolactone (PCL).

Still other embodiments are directed to methods for removing fluids from a wound site. Certain embodiments of a method for removing a fluid from a wound site may comprise the steps of: obtaining a wound insert comprising an open-celled reticulated foam member comprising a porous film layer, the porous film layer comprising a film thickness; and at least a channel comprising a channel depth, the channel depth being equal to or greater than the film thickness; obtaining a patient having a wound; inserting the wound insert into the wound such that the porous film layer faces the wound; applying a drape such that the wound insert is disposed between the drape and the wound, and the drape is coupled to skin adjacent the wound; obtaining a vacuum source coupled to the wound insert; and applying negative pressure to the wound insert.

Other embodiments may comprise the steps of obtaining a wound insert comprising an open-celled reticulated foam member comprising a porous film layer, the porous film layer comprising a film thickness; and at least a channel comprising a channel depth, the channel depth being equal to or greater than the film thickness; obtaining a patient having a wound; inserting the wound insert into the wound such that the porous film layer faces the wound; applying a drape such that the wound insert is disposed between the drape and the wound, and the drape is coupled to skin adjacent the wound; and actuating a fluid source coupled to the wound insert such that fluid is delivered to the wound insert The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a wound-treatment method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises one of the present wound inserts and a drape, the wound dressing includes the specified elements but is not limited to having only those elements. For example, such a wound dressing could also include a connection pad configured to be coupled to a negative pressure wound therapy (NPWT) apparatus (e.g., including a vacuum source and/or a fluid source).

Further, a device or structure that is configured in a certain way is configured in at least that way, but it can also be configured in other ways than those specifically described.

Referring now to FIGS. 1-3B, embodiments of a foam dressing 8 and methods for manufacturing such a dressing are shown.

Figure 1:
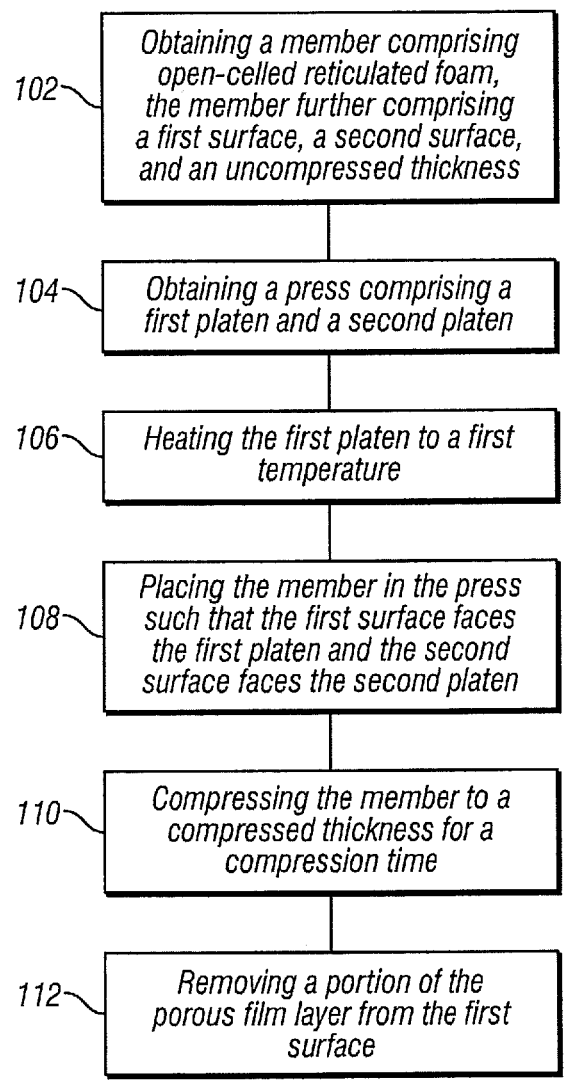
FIG. 1 illustrates an embodiment of a method of making a wound insert.
Figure 2A:
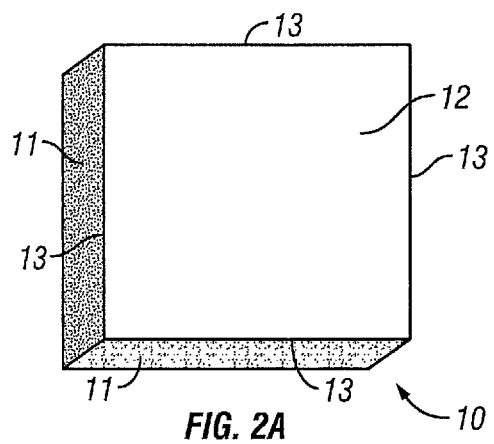
FIG. 2A illustrates a perspective view of an embodiment of a foam member.
Figure 2B:
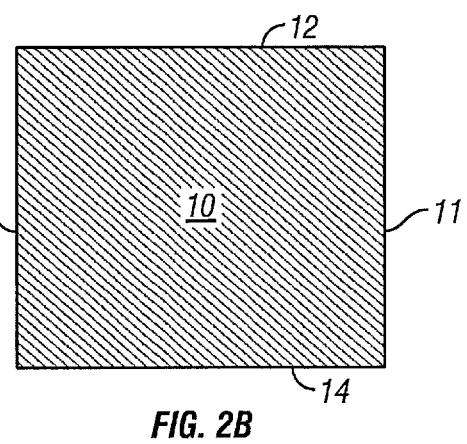
FIG. 2B illustrates a side view of embodiment of a foam member.

FIGS. 2A and 2B depict perspective and side views of an open-celled reticulated foam member 10, having a first surface 12, a second surface 14, sides 11, and edges 13. Foam member 10 may be of any suitable shape, including a rectangular prism or a cylinder. In certain applications, foam member 10 may comprise a regular or irregular polygon having a depth, depending on the shape of the wound into which it is intended to be inserted. One of skill in the art will appreciate that the dimensions of foam member 10 in the accompanying figures have been exaggerated for clarity.

An open-celled reticulated foam has a netlike microstructure, with few if any closed cells. In certain embodiments, the porosity can range from 95%-98%, though less porous or more porous foams may be used. In certain embodiments, foam member 10 may comprise a polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, foam member 10 may comprise a bioabsorbable polymer, examples of which include polylactic acid, polylactide (PLA), polyglycolic acid, polyglycolide (PGA), and polycaprolactone (PCL). Methods of manufacturing open-celled reticulated foam are well known. Open-celled reticulated foam is commercially available from a variety of sources, including Kinetic Concepts, Inc., San Antonio, Tex.

In the embodiments shown in FIGS. 2A and 2B, first surface 12, second surface 14, and sides 11 of foam member 10 are unfinished. In other words, reticulated cells extend to all surfaces of the foam member. In certain applications, these unfinished surfaces allow negative pressure to be applied to the wound site and encourage granulation tissue to grow into the foam member, which may be desirable depending on the nature of the wound. In other applications, however, the formation of granulation tissue in the foam member may complicate or impede the healing process, even though it would be desirable to provide negative pressure to the wound site. As discussed in more detail below, certain surfaces may be left unfinished if it is desirable that granulation tissue grows into them.

Figure 3A:
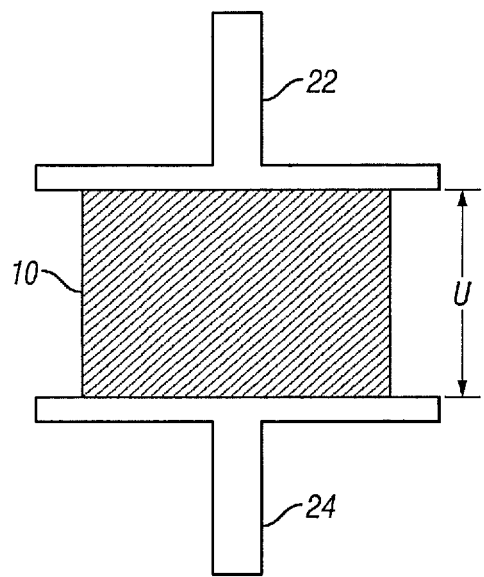
FIG. 3A illustrates a schematic view of an embodiment of an uncompressed foam member in a press.
Figure 3B:
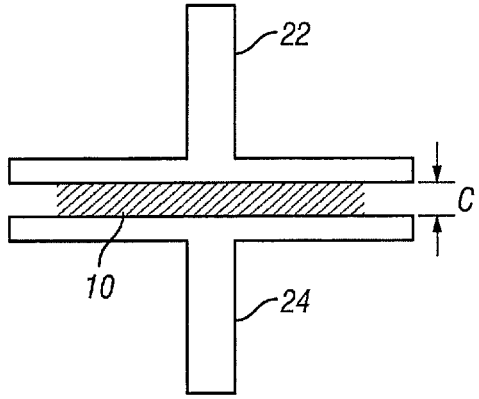
FIG. 3B illustrates a schematic view of an embodiment of a compressed foam member in a press.

Referring now to FIGS. 3A and 3B, foam member 10 having an uncompressed thickness U is shown schematically between a first platen 22 and a second platen 24 in a press (not shown). Suitable presses are commercially available from numerous sources, including Carver Press, Wabash, Ind. First platen 22, second platen 24, or both may be capable of being heated to a specified temperature. In the embodiment shown, first platen 22 is heated to a specified temperature. In certain embodiments, the temperature may range between 160° C. and 180° C., depending on the foam used. Foam member 10 is placed in the press such that first surface 12 faces first platen 22, and second surface 14 faces second platen 24. The platens 22, 24 are brought together, compressing foam member 10 to a compressed thickness C. Compressed thickness C of foam member 10 is a fraction of uncompressed thickness U. In certain embodiments, compressed thickness C may be less than one-tenth, one-ninth, one-eighth, one-seventh, one-sixth or one-fifth uncompressed thickness U.

Porous film layer 16 is formed by applying heat and pressure to the foam member; such application of heat and pressure is sometimes known as "felting." Porous film layer 16 is sometimes known as a "felted layer." In such a process, foam member 10 is held in a compressed position between first platen 22 and second platen 24 for a specified period of time. In certain embodiments, the period of time ranges between 15 and 30 minutes, though the time period may be more or less depending on the material used for foam member 10. Generally, the lower the temperature of the platen, the longer foam member 10 must be held in compression. Overheating the platen, or applying pressure for too long, may risk damaging foam member 10 by charring or burning it.

Figure 4:
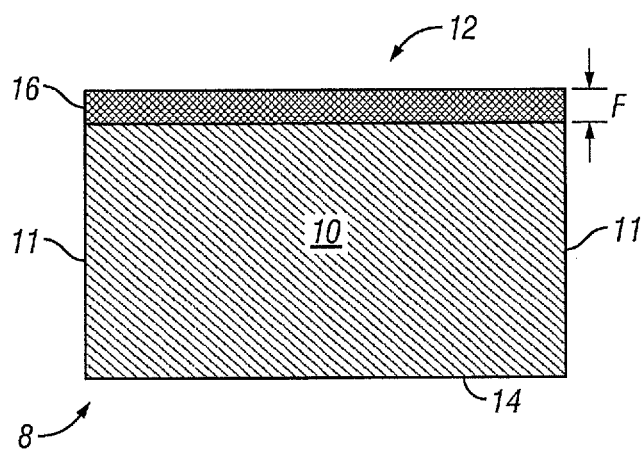
FIG. 4 illustrates a side view of an embodiment of a wound insert.

After the specified time period has elapsed, foam member 10 may be removed from the press. As shown in FIG. 4, the pressure and heat will form a porous film layer 16 on first surface 12 having thickness F. Porous film layer 16 is integral with foam member 10. In other words, porous film layer 16 and foam member 10 form a single unitary body. Porous film layer 16 will be comparatively smoother than any unfinished or non-felted surface, such as second surface 14 in the embodiment shown. Further, the pores in porous film layer 16 are substantially smaller than the pores throughout foam member 10 in general or on any non-felted side.

In certain embodiments, it may be desirable to form a porous film layer on second surface 14 of foam member 10. Those of skill in the art will understand that it is possible to form porous film layers on first surface 12 as well as on second surface 14. Methods of forming a porous film layer 16 include heating both platens before compressing foam member 10, or first compressing and heating one side then compressing and heating the other side. In such embodiments, the porous film layer formed on second surface 14 is integral with foam member 10. That is, the porous film later formed on second surface 14 and foam member 10 comprise a single unitary body.

Figure 5A:
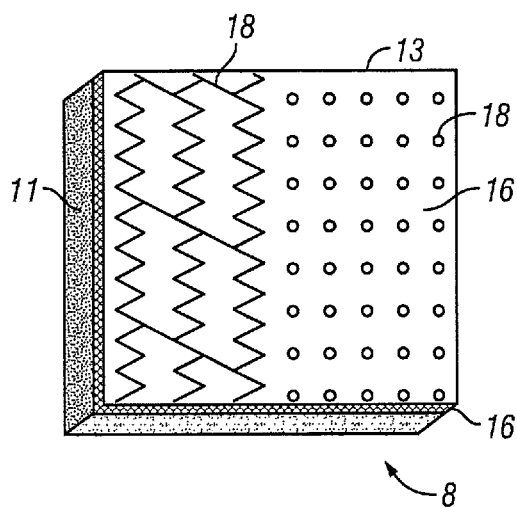
FIG. 5A illustrates a perspective view of an embodiment of a wound insert comprising a plurality of channels.
Figure 5B:
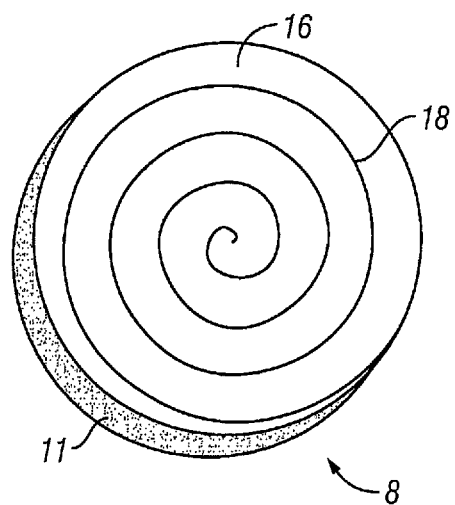
FIG. 5B illustrates a perspective view of an embodiment of a wound insert comprising a channel.
Figure 6A:
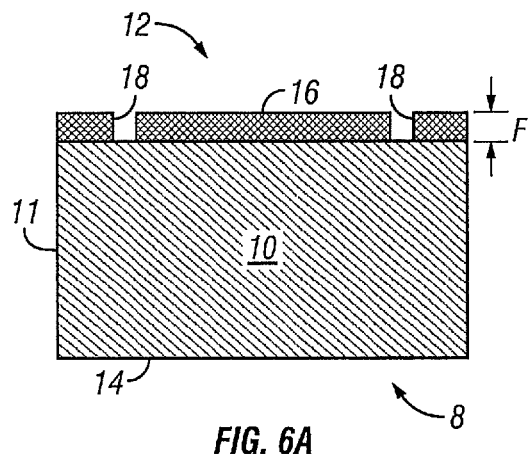
FIG. 6A illustrates a side view of a wound insert comprising a plurality of channels.
Figure 6B:
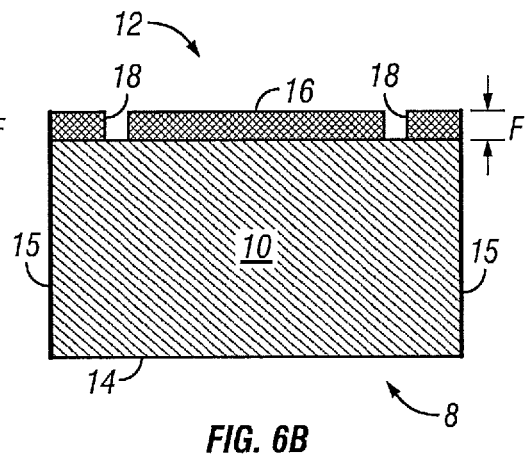
FIG. 6B illustrates a side view of a wound insert comprising a plurality of channels.

Perspective views and side views of various embodiments of wound insert 8 are shown in FIGS. 5A-6B. First surface 12 of wound insert 8 comprises porous film layer 16 that intersects with sides 11 at edges 13, as well as one or more channels 18. Channels 18 may take a variety of shapes, including straight, curved, zig-zag, spiral, circular, or any fanciful shape. As shown in FIG. 5A, channels 18 may run to edge 13, or may be self-contained on first surface 12. The exact shape of channels 18 may be configured for optimal fluid removal or fluid instillation at the wound site. As shown in FIGS. 6A and 6B, the depth of channels 18 may be about equal to thickness F of film layer 16. In other embodiments, the depth of channels 18 may be greater than thickness F of film layer 16. And in still other embodiments, the depth of channels 18 may be less than the thickness F of film layer 16.

In certain embodiments, channels 18 may be formed on first surface 12 by removing portions of porous film layer 16. In some embodiments, portions of porous film layer 16 may be removed with a laser cutter (not shown). In one example, the desired channel pattern is drawn in a CAD program. The channel pattern may be transmitted to a computer-controlled laser cutter, which then applies a laser beam to the porous film layer 16 of the wound insert 8. An advantage of using a laser cutter instead of other methods to remove material is that the focal depth of the laser is easily adjusted, and thus the depth of channels 18 may be precisely controlled. A laser may be more easily adjusted to remove material only from porous film layer 16, and not from foam member 10. Additionally, a laser with an adjustable focal depth may more easily create channels 18 having different depths: for example, some channels 18 may have a depth equivalent to thickness F of porous film layer 16, while other channels 18 may have a depth greater than F. Other material-removal processes may be used, however. For example, a water jet cutter, a die press, or etching may be used to remove material from porous film layer.

Channels 18 may also be formed in other ways, such as by molding. A mold with the desired channel pattern may be coupled to one or both platens during the heating and compression steps. In certain embodiments, use of a mold will prevent porous film from being formed in the channels 18. In other embodiments, channels 18 may comprise a layer of porous film 16.

Referring again to FIGS. 6A and 6B, cross-sectional views of a wound insert are shown. As shown in FIG. 6A, in some embodiments, sides 11 are unfinished, such that the open-celled reticulated foam member 10 is exposed. As shown in FIG. 6B, in other embodiments, sides 11 are finished with a seal or seam 15. Sides 11 or second surface 14 may be finished or unfinished depending on the desired application. Leaving sides 11 or surface 14 unfinished may encourage granulation tissue growth into foam member 10. Sealing or seaming or otherwise finishing sides 11 or surface 14 will prevent such tissue growth. Granulation tissue growth is desirable in some instances but not in others.

Figure 7:
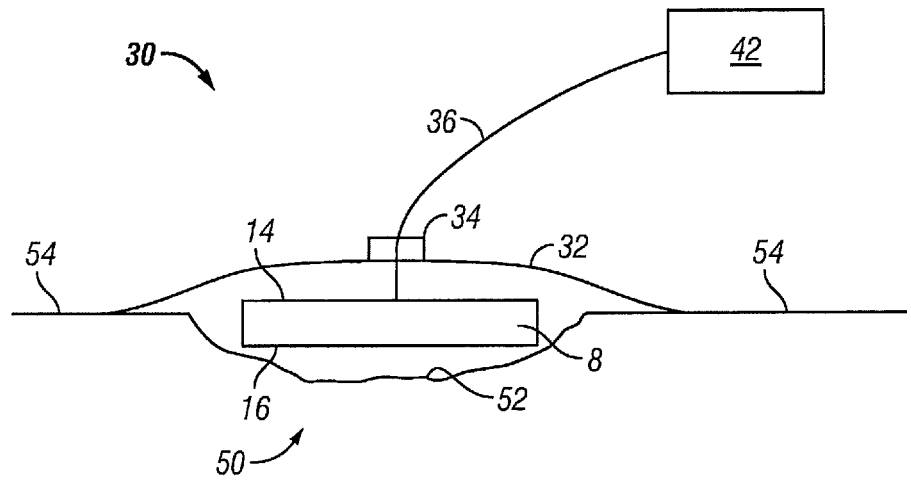
FIG. 7 illustrates a schematic diagram of a wound insert in a wound.

Referring now to FIG. 7, wound insert 8 is shown as part of a wound treatment system 30. In the embodiment shown, wound insert 8 is shown placed in wound 50 of a patient (not shown) such that first surface 12 comprising porous film layer 16 and channels 18 faces the wound surface 52. In other embodiments, wound insert 8 may comprise more than one porous film layer 16 disposed on, for example, second surface 14; these additional porous film layer(s) 16 may or may not include channels 18.

A drape 32 is placed over wound 50 and wound insert 8 such that wound insert 8 is between drape 32 and wound 50. Drape 32 is coupled to the skin 54 of the patient. Wound insert 8 is coupled to a wound treatment apparatus 42 by conduit 36. Apparatus 42 may comprise a vacuum source configured to apply negative pressure to wound insert 8 through conduit 36. Apparatus 42 may further comprise a fluid source configured to deliver a fluid through conduit 36 to wound insert 8. For example, apparatus 42 may comprise a pump configured to pump a fluid through conduit 36 to wound insert 8. Examples of such fluids include a medicinal fluids, antibacterial fluids, or irrigation fluids. Various wound therapy systems and components are commercially available through and/or from KCI USA, Inc. of San Antonio, Tex., U.S.A.

Conduit 36 can comprise a single lumen conduit (e.g., switched between a vacuum source and/or a fluid source) or can comprise multiple single-lumen conduits or a multi-lumen conduit such that, for example, fluid can be delivered and/or negative pressure can be applied to wound insert 8 individually or simultaneously. Or conduit 36 can comprise multiple lumens (e.g., as in a single conduit with a central limit for application of negative pressure and/or fluid delivery and one or more peripheral lumens disposed adjacent or around the central lumen such that the peripheral lumens can be coupled to a pressure sensor to sense and/or detect a pressure or negative pressure between drape 32 and wound surface 52. In the embodiment shown, system 30 further comprises a wound dressing connection pad 34 configured to be coupled (and is shown coupled) to conduit 36. One example of a suitable connection pad 36 is the "V.A.C. T.R.A.C.® Pad," commercially available from KCI USA, Inc. of San Antonio, Tex., U.S.A. One example of a suitable drape 32 includes the "V.A.C.® Drape" commercially available from KCI USA, Inc. (and its affiliates) of San Antonio, Tex., U.S.A.

Channels 18 provide a path of lower resistance between second surface 14 through foam member 10 as compared to the path through porous film 16. Thus, when a fluid is instilled through wound insert 8, most or all of the fluid will tend to flow into wound 50 through channels 18. And conversely, when fluids are being removed from wound 50, much or all of the fluid will flow up through channels 18, through foam member 10, and into conduit 36.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

We claim:

1. A wound insert comprising:
   a foam member having a top surface and a bottom surface, the foam member comprising open-celled foam;
   a felted layer configured to allow passage of negative pressure, the felted layer forming at least a portion of the bottom surface;
   at least one channel in the felted layer, wherein the at least one channel comprises a channel depth, the channel depth being at least equal to a thickness of the felted layer; and
   wherein the wound insert is configured to be disposed between a wound of a patient and a drape coupled to skin adjacent to the wound.

2. The wound insert of claim 1, wherein the thickness of the felted layer is less than about one-fifth a thickness of the foam member.

3. The wound insert of claim 1, wherein the at least one channel has a circular shape.

4. The wound insert of claim 1, wherein the foam member and the felted layer each comprise pores, and wherein the pores in the felted layer are substantially smaller than the pores in the foam member.

5. The wound insert of claim 1, wherein a thickness of the foam member is between the top surface and the bottom surface of the foam member, and wherein the at least one channel is in fluid communication between the top surface and the bottom surface through the thickness of the foam member.

6. The wound insert of claim 1, wherein the at least one channel is defined by material removed from the felted layer.

7. A wound insert comprising:
 a felted porous foam layer comprising a layer thickness; and
 at least one channel in the felted porous foam layer, wherein the at least one channel comprises a channel depth, the channel depth being at least equal to the layer thickness;
 wherein the wound insert is configured to be disposed between a wound of a patient and a drape coupled to skin adjacent to the wound.

8. The wound insert of claim 7, wherein the felted porous foam layer is configured to allow the passage of negative pressure and to inhibit tissue in-growth.

9. The wound insert of claim 7, wherein the at least channel has a circular shape.

10. The wound insert of claim 7, further comprising a foam member, wherein the felted porous foam layer forms at least one surface of the foam member.

11. The wound insert of claim 7, further comprising a foam member, wherein the foam member and the felted porous foam layer each comprise pores, and wherein the pores in the felted porous foam layer are substantially smaller than the pores in the foam member.

12. The wound insert of claim 7, further comprising a foam member having a first surface, a second surface, and a thickness between the first surface and the second surface, wherein the at least one channel is in fluid communication between the first surface and the second surface through the thickness of the foam member.

13. The wound insert of claim 7, wherein the at least one channel is defined by material removed from the felted porous foam layer.

14. The wound insert of claim 7, wherein the channel depth is greater than the layer thickness.

* * * * *